(12) United States Patent  
Schnitzler et al.

(10) Patent No.: US 8,747,298 B2  
(45) Date of Patent: Jun. 10, 2014

(54) PROBE MANIPULATOR

(75) Inventors: Uwe Schnitzler, Tübingen (DE); Martin Hagg, Wannweil (DE)

(73) Assignee: Erbe Elektromedizin GmbH, Tübingen (DE)

( * ) Notice: Subject to any disclaimer, the term of this patent is extended or adjusted under 35 U.S.C. 154(b) by 1231 days.

(21) Appl. No.: 12/280,640

(22) PCT Filed: Feb. 13, 2007

(86) PCT No.: PCT/EP2007/001248  
§ 371 (c)(1),  
(2), (4) Date: Aug. 25, 2008

(87) PCT Pub. No.: WO2007/098857  
PCT Pub. Date: Sep. 7, 2007

(65) Prior Publication Data  
US 2009/0023990 A1  Jan. 22, 2009

(30) Foreign Application Priority Data  
Feb. 24, 2006 (DE) .......................... 10 2006 008 739

(51) Int. Cl.  
*A61B 1/00* (2006.01)  
*A61B 1/12* (2006.01)

(52) U.S. Cl.  
USPC .......................................... 600/106; 600/153

(58) Field of Classification Search  
USPC ......... 600/104, 106, 136, 154, 131, 137, 117, 600/153, 159–160  
See application file for complete search history.

(56) References Cited

U.S. PATENT DOCUMENTS

| 4,726,369 A | 2/1988 | Mar |
| 4,829,999 A | 5/1989 | Auth |
| 5,207,675 A | 5/1993 | Canady |
| 5,645,519 A * | 7/1997 | Lee et al. ...................... 600/114 |
| 5,720,745 A | 2/1998 | Farin et al. |
| 6,004,263 A * | 12/1999 | Nakaichi et al. .............. 600/176 |
| 6,477,402 B1 | 11/2002 | Lynch et al. |
| 6,606,515 B1 * | 8/2003 | Windheuser et al. ......... 600/434 |
| 6,746,466 B2 * | 6/2004 | Eidenschink et al. ........ 606/194 |
| 6,827,683 B2 * | 12/2004 | Otawara ........................ 600/123 |
| 6,830,545 B2 | 12/2004 | Bendall |
| 7,198,599 B2 * | 4/2007 | Goto et al. .................... 600/154 |
| 2002/0103418 A1 | 8/2002 | Maeda et al. |
| 2005/0159764 A1 * | 7/2005 | Kasahara et al. ............. 606/159 |

FOREIGN PATENT DOCUMENTS

DE  198 26 746  11/1999

OTHER PUBLICATIONS

Roche Lexikon Medizin, 4. Auflage, 1998, S. 1560, S. 468 (Definition: Sonde/Endoskop).

* cited by examiner

*Primary Examiner* — Alireza Nia  
(74) *Attorney, Agent, or Firm* — Dickstein Shapiro LLP

(57) ABSTRACT

A probe manipulator which has a grip device that can be held by a user in order to facilitate manipulation of a probe when the latter has been inserted into a channel of an endoscope. Connection devices are provided for releasably connecting the grip device to the probe in such a way that the probe may be rotated or displaced by rotation or displacement of the grip device. The connection device is connectable such that the probe need not be fed through the grip device, but that the grip device may be placed at any point along the length of the probe.

13 Claims, 2 Drawing Sheets

PROBE MANIPULATOR

FIELD OF THE INVENTION

The invention relates to a probe manipulator, and in particular to a probe manipulator which has a grip device that can be held by a user in order to facilitate manipulation of a probe when the latter has been inserted into a channel of an endoscope and having connection devices which releasably connects the grip device to the probe.

BACKGROUND OF THE INVENTION

In endoscopic operations, probes are often introduced into a working channel of an endoscope in such a way that their distal ends are located in the field of view of the endoscope optics, in order to act on a patient's tissue using the probe. One example of such a probe is described in U.S. Pat. No. 5,720,745 (assigned to Erbe Electromedizin GmbH). This probe is used in the coagulation of tissue using high-frequency current, which is supplied to the tissue through an argon plasma. In order to move the probe inside the endoscope or inside the working channel thereof, the operator holds the probe near the access aperture to the working channel of the endoscope. Since the probes are very thin, this procedure requires a high degree of "feeling."

U.S. Pat. No. 5,207,675 describes a probe for argon-plasma coagulation in which a hand grip is attached to the proximal end of the probe in order to move the probe inside the working channel. In this case, however, the probe must be manufactured to fit the endoscope with which it is designed to be used.

Accordingly, a probe manipulator that enables the probe to be handled precisely and simply by the operator is desirable.

SUMMARY

Disclosed embodiments include a probe manipulator having a grip device that can be gripped by a user to manipulate a probe introduced into a working channel of an endoscope and a connection device to releasably connect the grip device to the probe in such a way that the probe is rotated or displaced upon rotation or displacement of the grip device.

In disclosed embodiments, the probe itself is not provided with a grip, but rather that a separate probe manipulator is provided, which can be handled separately from the probe but can be connected to it, in order to allow manipulation of the probe during a surgical procedure. This allows the manipulator to be connected to different probes according to the required application at any given time. Additionally, the probe does not need to be manufactured specifically to fit the endoscope with which it is being used. This allows, for example, the probe to be very long so that an extension cable or similar is not required in order that the pertinent appliance for supplying high frequency current, as well as inert gas, can be positioned at a sufficient distance from the operative field, while still allowing the grip device to be attached very close to the aperture to the working channel, so that, when manipulating, particularly when pushing the probe, it cannot bend. This enables the grip device to act as a buffer, so that the probe cannot be introduced too far and thus is not able to project too far beyond the distal end of the endoscope. Thus, the disclosed embodiments also provide an additional safety measure.

In a preferred embodiment, the connection devices are designed in such a way that the probe, at a section distanced from both the distal and the proximal ends, can be releasably connected to the grip device while the probe is being used. This allows the grip device to be connected to the probe at a required position, without requiring any awkward threading into the grip. In addition, when changing probes, the same grip device can be removed from the probe to be replaced and then connected to the new probe.

Control mechanisms are preferably provided on the grip devices and are designed in such a way that the user can guide medical appliances connected to the probe by using the control mechanisms. Thus, using the fingers of the hand with which the probe is being moved, the user can, for example, actuate a suction device, and can control the parameters by which the probe is operated, e.g., a high-frequency coagulation current. A foot switch can therefore be dispensed with or, if present, can be used for other purposes. Therefore, a particularly logical arrangement of actuating devices for the appliances is thereby possible, together with which the probe is operated.

The grip device is preferably designed to be rotationally symmetrical and to be connected to the probe in such a way that the probe can be rotated about its longitudinal axis without the user having substantially to alter the grip position. This considerably facilitates the handling ability of the probe manipulator.

The connection devices can be of various types, such as e.g., screw connections or the like. In a preferred embodiment the connection devices are designed as clamping devices, which can be used with one hand. During the operation, the operator can thus displace the connection device on the probe or position it some other way, as desired.

BRIEF DESCRIPTION OF THE DRAWINGS

In the following, the invention will now be described in more detail with reference to an exemplary embodiment, which will be explained in more detail with reference to the enclosed drawings.

DETAILED DESCRIPTION OF THE INVENTION

Figure 1:
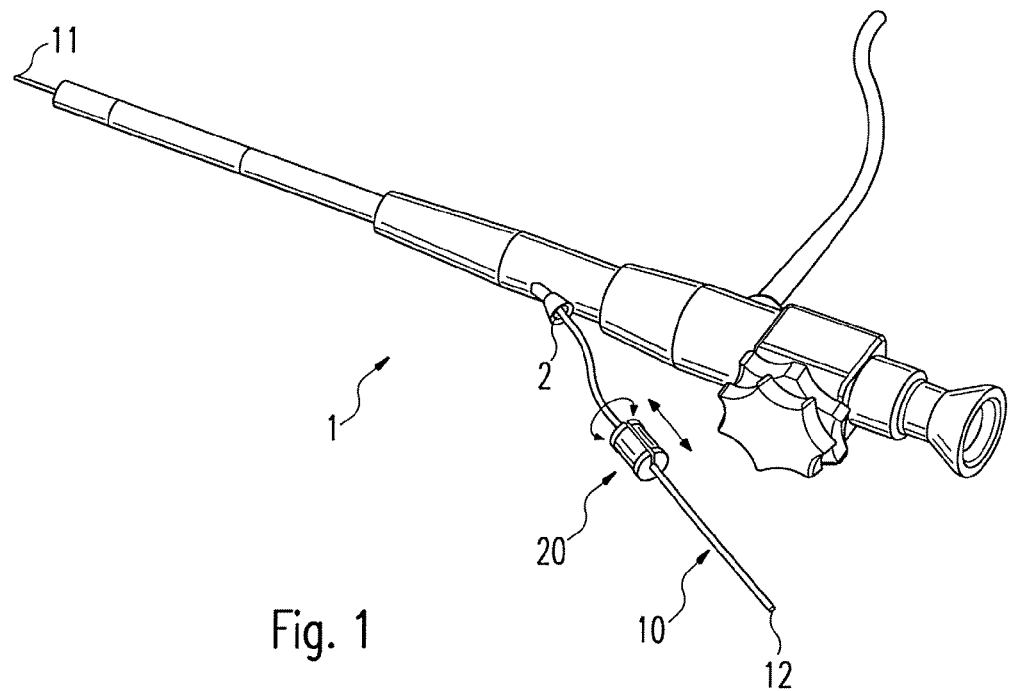
FIG. 1 is a perspective view illustrating an exemplary embodiment.

In the following description the same reference numerals are used for identical and identically functioning parts.

Referring to FIG. 1, an endoscope 1 includes an aperture 2 in which a working channel is provided. A probe 10 is pushed into this working channel in such a way that its distal end 11 projects beyond the end of the working channel and its proximal end 12 extends far enough out of the aperture 2 of the working channel, that it can be connected to an actuating appliance, e.g. a source for rinsing fluid, a suction device or an appliance for argon plasma coagulation.

A grip device 20 is placed on and connected to the probe 10. As indicated by the arrows in FIG. 1, the grip device 20 is connected in such a way that it is possible for the probe 10 to be longitudinally displaced (e.g., to be further introduced into the working channel or to be drawn out of it) as well as rotated inside the working channel.

Figure 2:
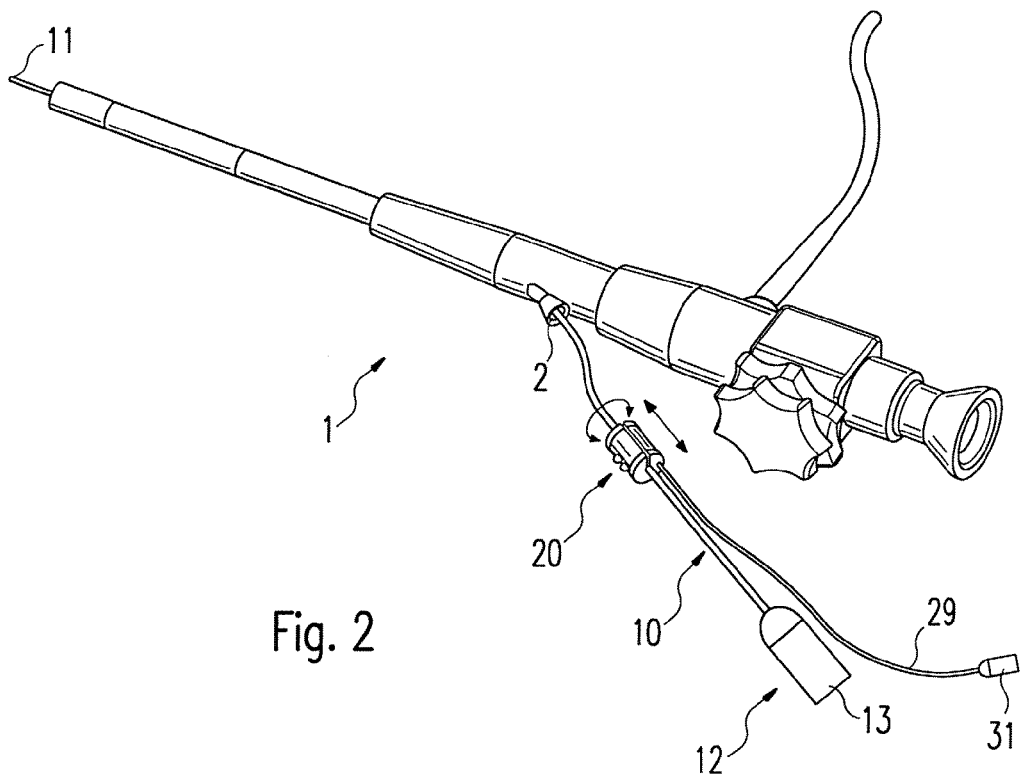
FIG. 2 is a perspective view illustrating another exemplary embodiment of the invention.

The embodiment shown in FIG. 2 differs from that according to FIG. 1 in that the grip device 20 is additionally connected to a connection cable 29, which can be connected by a plug 31 to an appliance, in particular to the appliance by which the probe 10 is operated. Furthermore, FIG. 2 also shows a plug 13, via which the proximal end 12 of the probe 10 can be joined to the actuating appliance provided for the probe 10.

Figure 3:
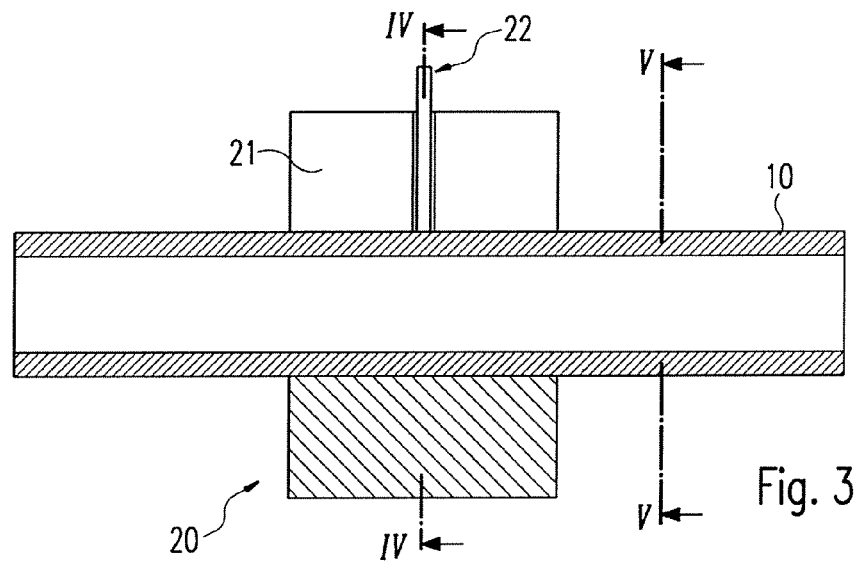
FIG. 3 is a longitudinal section through a probe manipulator with clamped probe tube.
Figure 4:
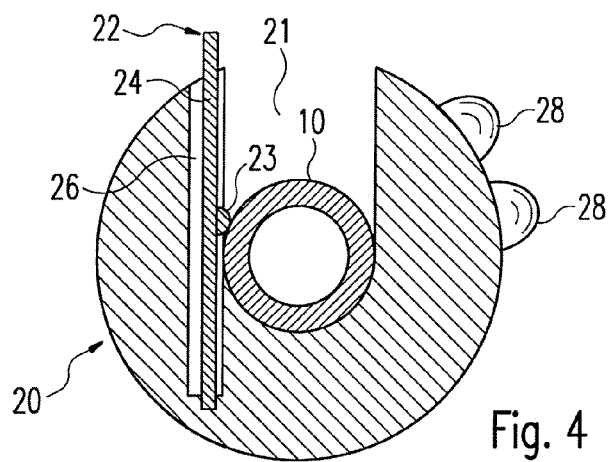
FIG. 4 is a cross-sectional view along line IV-IV of FIG. 3.
Figure 5:
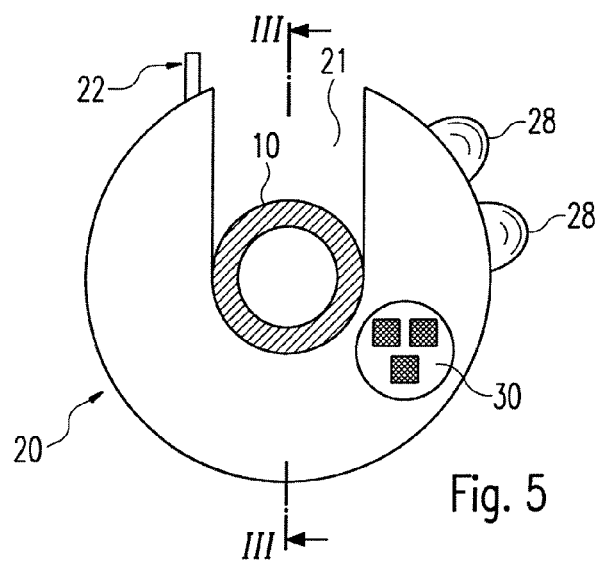
FIG. 5 is a cross-sectional view along line V-V of FIG. 3.

The grip device 20 is hereinafter described in more detail with reference to FIGS. 3-5. In the embodiment of the invention shown here in simplified form, which corresponds to the grip device as shown to FIG. 2, the grip device 20 has a substantially cylindrical design and includes a slot 21, which has a base that matches the tubular shape of the probe 10 and is designed to be sufficiently deep for the probe 10 to be located in the center of the cylindrical grip device 20.

The slot 21 is open to the exterior in such a way that the grip device 20 can be slid onto the probe 10 at any point along the total length of the probe 10, so that the probe 10 does not have to be threaded through an aperture using one of its ends 11 or 12.

A simple clamping device can suffice to connect the grip device 20 to the probe 10. In the embodiment shown in FIGS. 3-5, the clamping device consists of a flexible rod 24, which includes a clamping projection 23 and which projects with a clamping head 22 out of a recess 26 in the grip device 20. The clamping head 22 can be displaced (e.g., in FIG. 4 to the left side in an counter-clockwise direction), so that the flexible rod 24 bends and the clamping projection 23 releases the probe 10. In this state, the grip device 20 can be either displaced along the probe 10, rotated or completely removed from the probe 10.

Furthermore, the grip device 20 is equipped with actuating switches 28 (FIGS. 2-5) which are connected via the connection cable 29 (this can be connected via a plug to a socket 30 on the grip device) and the plug 31 to an actuating appliance for the probe 10. The actuating appliance (e.g. a high frequency generator with an argon source) can thus be controlled by the operator via actuating switch 28 using the same hand that is holding the grip device 20 and manipulating the probe 10 in the working channel of the endoscope 1.

The invention claimed is:

1. A probe manipulator comprising:
    a substantially cylindrical grip device; and
    a connection device for releasably connecting the grip device to a probe that has been inserted into a working channel of an endoscope,
    wherein the grip device comprises a radial slot therein, the radial slot being configured to accept the probe radially therein and wherein the radial slot is radially open to an exterior of the grip device such that the grip device can be slid onto the probe at any point along an entire length thereof and the radial slot is sufficiently deep for the probe to be located in a center of the cylindrical grip device, and
    wherein the connection device comprises a flexible rod disposed in a recess in the grip device, the recess being located adjacent to the radial slot in the grip device, and a clamping projection on the flexible rod,
    wherein the flexible rod is configured to bend in a direction away from the radial slot, and wherein the clamping projection is attached to the flexible rod such that when the flexible rod is bent, the clamping projection releases the probe, and when the flexible rod is not bent, the clamping projection holds the probe in place within the radial slot.

2. The probe manipulator according to claim 1, wherein the connection device is configured such that the connection device can be releasably connected to the probe at a section distanced from its ends.

3. The probe manipulator according to claim 1, wherein the grip device further comprises control mechanisms which are configured such that a user can guide medical appliances connected to the probe using the control mechanisms.

4. The probe manipulator according to claim 1, wherein the grip device is connected to the probe such that the probe can be rotated about its longitudinal axis without a user having to substantially alter the grip position.

5. The probe manipulator according to claim 1, wherein the connection device is a clamping device.

6. The probe manipulator according to claim 5, wherein the connection device is configured to be used by a user with a single hand.

7. The probe manipulator according to claim 1, further comprising a cable connected to the grip device, wherein the cable is configured to connect an appliance by which the probe is operated to the probe.

8. The probe manipulator according to claim 1, wherein the grip device allows a user to manipulate the probe, such that the probe is longitudinally displaced or rotated by respectively longitudinally displacing or rotating the grip device.

9. The probe manipulator according to claim 1, wherein the connection device further comprises a clamping head located at an end of the flexible rod which projects out of the recess in the grip device, wherein the flexible rod is bent by displacing the clamping head.

10. A probe manipulator comprising:
    a substantially cylindrical grip device that can be held by a user in order to manipulate a probe that has been inserted into a working channel of an endoscope; and
    a connection device for releasably connecting the probe to the grip device,
    wherein the grip device comprises a radial slot therein, the radial slot being configured to accept the probe radially therein and wherein the radial slot is radially open to an exterior of the grip device such that the grip device can be slid onto the probe at any point along an entire length thereof and the radial slot is sufficiently deep for the probe to be located in a center of the cylindrical grip device, and
    wherein the connection device comprises a flexible rod disposed in a recess in the grip device, the recess being located adjacent to the radial slot in the grip device, and a clamping projection on the flexible rod,
    wherein the flexible rod is configured to bend in a direction away from the radial slot, and wherein the clamping projection is attached to the flexible rod such that when the flexible rod is bent, the clamping projection releases the probe, and when the flexible rod is not bent, the clamping projection holds the probe in place within the radial slot.

11. The probe manipulator according to claim 10, wherein the connection device is configured such that the connection device can be releasably connected to the probe at a section distanced from its ends while the probe is in use.

12. The probe manipulator according to claim 10, wherein the grip device is rotationally symmetrical and is connected to the probe such that the probe can be rotated about its longitudinal axis without the user having to substantially alter the grip position.

13. The probe manipulator according to claim 10, wherein the connection device is a clamping device designed to be used single-handedly.

* * * * *